US006129696A

United States Patent [19]

Sibalis

[11] Patent Number: 6,129,696
[45] Date of Patent: *Oct. 10, 2000

[54] TRANSDERMAL DRUG APPLICATOR

[75] Inventor: Dan Sibalis, Stony Brook, N.Y.

[73] Assignee: Drug Delivery Systems Inc., New York, N.Y.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/445,577

[22] Filed: May 22, 1995

Related U.S. Application Data

[62] Continuation of application No. 08/126,124, Sep. 23, 1993, abandoned, which is a continuation of application No. 07/957,633, Oct. 6, 1992, abandoned, which is a continuation of application No. 07/703,593, May 20, 1991, abandoned, which is a continuation of application No. 07/315,191, Feb. 24, 1989, abandoned, which is a continuation of application No. 07/036,253, Apr. 9, 1987, abandoned, which is a division of application No. 06/778,183, Sep. 16, 1985, Pat. No. 4,708,716, which is a continuation-in-part of application No. 06/524,252, Aug. 18, 1983, Pat. No. 4,557,723, which is a continuation-in-part of application No. 06/660,192, filed as application No. PCT/US85/00080, Jan. 17, 1985.

[51] Int. Cl.[7] ................................................. A61N 1/30
[52] U.S. Cl. .............................................. 604/20; 607/149
[58] Field of Search .......................... 604/20; 607/149, 607/151

[56] References Cited

U.S. PATENT DOCUMENTS

| | | | |
|---|---|---|---|
| 3,677,268 | 7/1972 | Reeves | 128/803 |
| 4,164,226 | 8/1979 | Tapper | 128/798 |
| 4,215,696 | 8/1980 | Bremer et al. | 128/803 |
| 4,325,367 | 4/1982 | Tapper | 128/803 |
| 4,365,634 | 12/1982 | Bare et al. | 128/798 |
| 4,457,748 | 7/1984 | Lattin et al. | 604/20 |
| 4,474,570 | 10/1984 | Ariura et al. | 604/20 |
| 4,619,252 | 10/1986 | Ibbott | 604/20 |
| 4,767,401 | 8/1988 | Seiderman | 604/20 |

*Primary Examiner*—Mark Bockelman
*Attorney, Agent, or Firm*—Factor & Partners

[57] ABSTRACT

A transdermal drug applicator comprising at least two flexible drug reservoir units each having ends and being of a predetermined depth, and at least one medicament in at least one of the at least two reservoir units. Peripheral means are disposed entirely about the ends of the reservoir units for separating and insulating the reservoir units from each other along their predetermined depth to thereby preclude shorting out between the at least two reservoir units. Circuit means including battery means for electrically connecting the battery means to the at least two reservoir units, and means for covering the applicator including the at least two reservoir units leaving sides of the at least two reservoir units exposed for contacting the skin. The means for covering being flexible and having lip means including an underside for making contact with the skin when mounted on the skin with the at least two reservoir units substantially fully enclosed, so that when the applicator is mounted and retained on the skin, it deforms and conforms to the body in a complete electrical circuit through the skin is formed via the circuit means, and whereby the at least one medicament in at least one of the at least two drug reservoir units migrates out of the reservoir units through the skin into the blood stream of the patient by means of a mass transfer activity attributed to at least one mass transfer phenomenon selected from the group consisting of electrophoresis and electroosmosis.

31 Claims, 5 Drawing Sheets

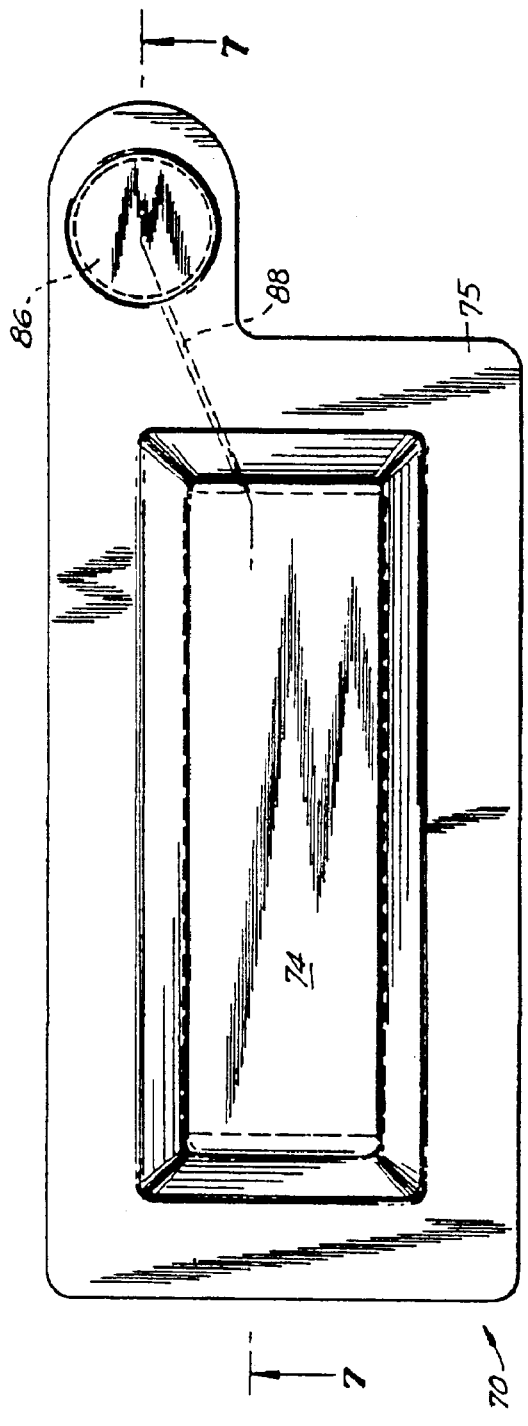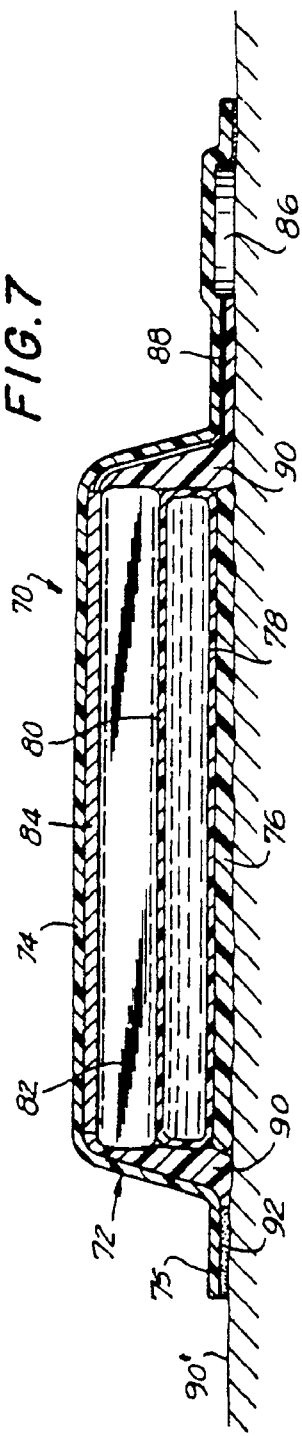

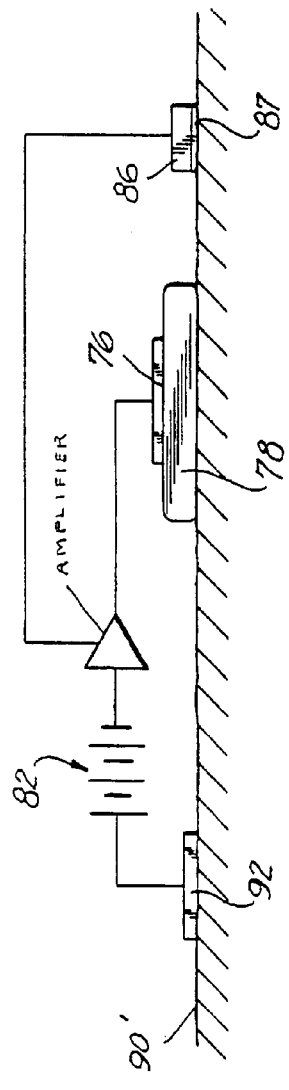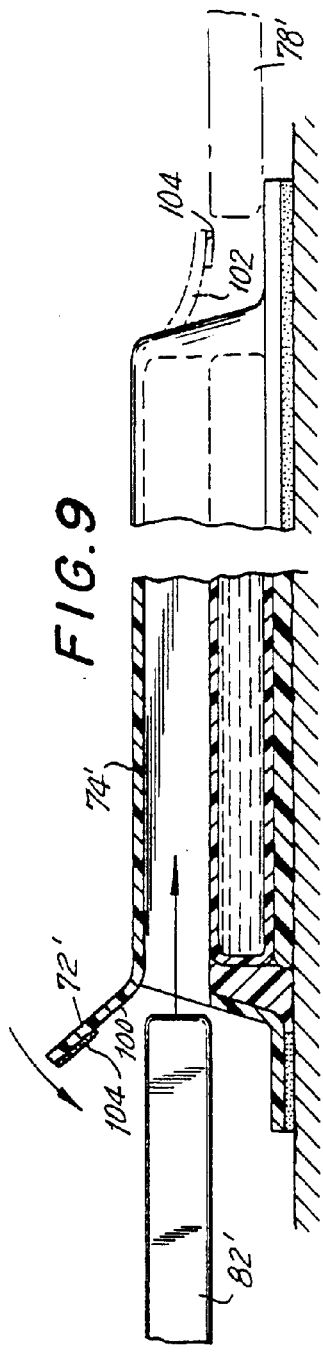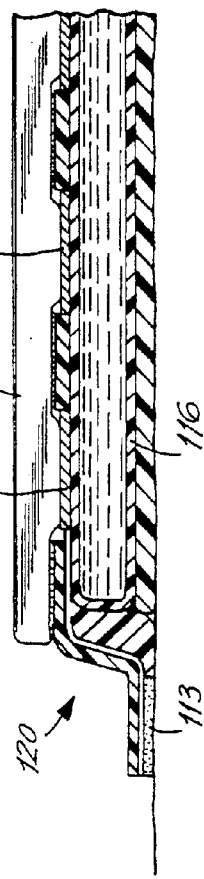

FIG. 14
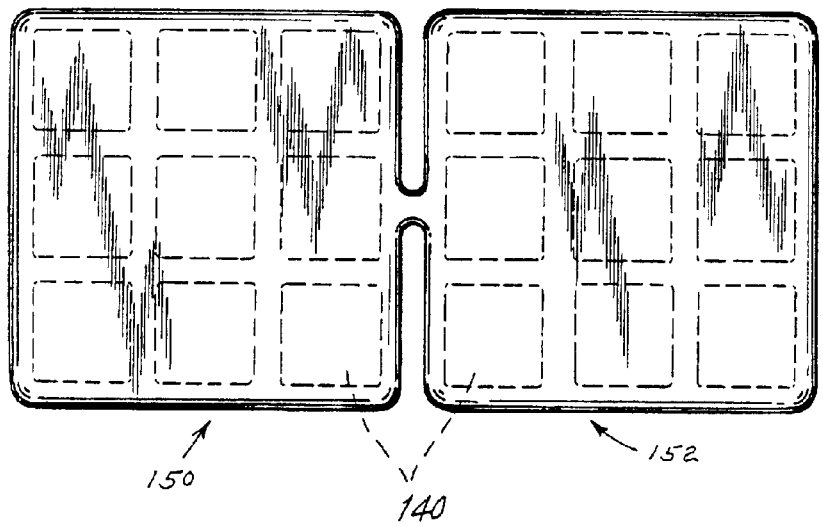
FIG. 15
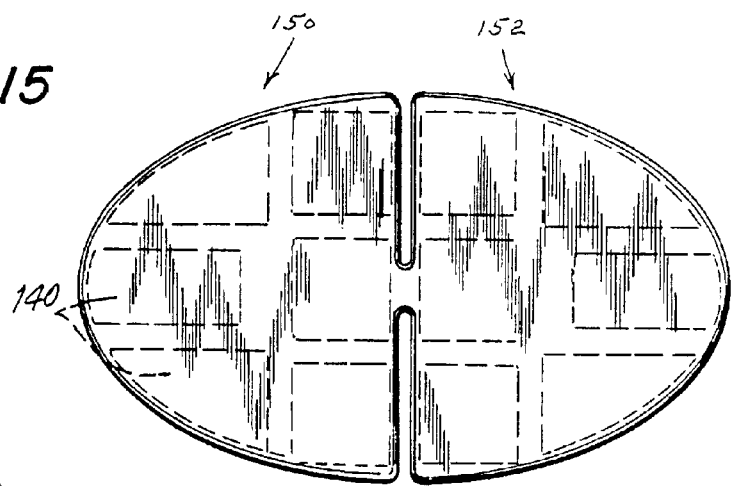
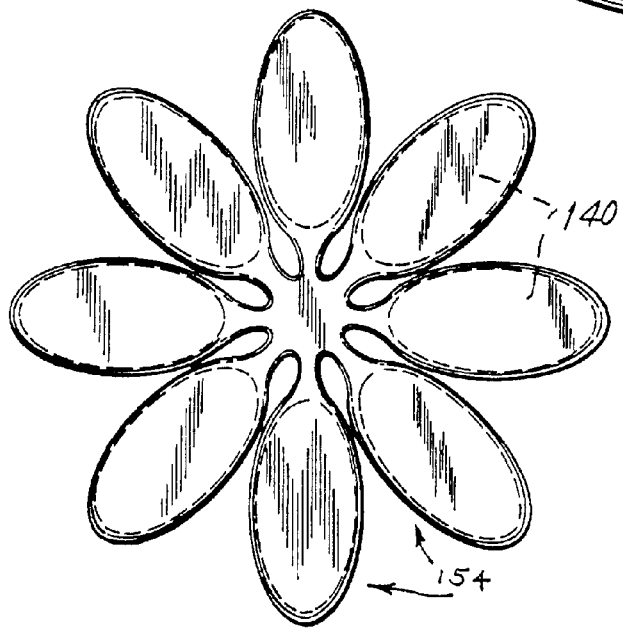
FIG. 16

TRANSDERMAL DRUG APPLICATOR

RELATED U.S. PATENT APPLICATIONS

This application is a continuation application of Ser. No. 08/126,124, Sep. 23, 1993, which is abandoned, which is a continuation application of Ser. No. 07/957,633, Oct. 6, 1992 now abandoned, which is a continuation application of Ser. No. 07/703,593, May 20, 1991 now abandoned, which is a continuation application of Ser. No. 07/315,191, Feb. 24, 1989 now abandoned, which is a continuation application of Ser. No. 07/036,253, Apr. 9, 1987, which is now abandoned, which is a divisional application of Ser. No. 06/778,183, Sep. 16, 1985, now U.S. Pat. No. 4,708,716, which is a division of Ser. No. 06/524,252, Aug. 18, 1983, now U.S. Pat. No. 4,557,723, and a continuation-in-part of Ser. No. 06/660,192, Oct. 12, 1984, now U.S. Pat. No. 4,622,031; and in which said parent case 06/778,183 was a U.S. designated filing from PCT/US85/00080 International application filed Jan. 17, 1985.

FIELD OF THE INVENTION

This invention relates to electrophoretic and/or electro-osmosis transcutaneous drug delivery. Specifically, this invention relates to a self-contained applicator for the transdermal drug delivery of medication. More particularly, such an applicator construction includes specialized structural configurations that compensate for skin stretch and movement, thus preventing loosening of the applicator and minimizing the chance of "burns" or other "tingling" sensations should wider fluctuations of current density occur; and one in which a third electrode is employed to regulate the pumped drug in accordance with a signal fed back into an amplified circuit.

BACKGROUND OF THE INVENTION

The delivery of medicament through a person's skin utilizing electrophoresis and/or electro-osmosis is one where the drug molecules in solution or suspension are made subject to an electric field, and in the case of electrophoresis, if the electrode having the same charge as that of the ionic molecules is above the solution adjacent the skin which is the site of administration, the ions will be repelled and migrate through the skin into the blood stream; whereas in the case of electro-osmosis, a solution of water is attracted to the negative electrode, and thus any electric current flowing through a porous membrane causes a flow therethrough. Such electrochemical processes, although similar in end result do, however, function together, but separately or independently, in pumping and/or delivering a drug or other medication transdermally.

U.S. Pat. No. 3,547,107 to Chapman et al shows a self-contained chest mounted heart tachycardia detector, and an insertable replaceable battery is disclosed, and the device is held to the patient by a separate piece of tape.

U.S. Pat. No. 4,008,721 to Burton discloses a tape electrode per se for transmitting electrical signals through the skin. A silver metal containing electrically conductive layer is disposed over an adhesive layer.

In U.S. Pat. No. 4,325,367 to Tapper, there is disclosed a iontrophoretic treatment device which is self-contained in a fixed structural housing. Metal electrodes, particularly a stainless steel cathode and an aluminum anode are connected to respective adjacently mounted porous moisture absorbent pads, and are wire-connected to a battery. The device is not adhered to the user's body, but rather the user physically holds the device in place against the body.

U.S. Pat. No. 4,419,091 to Behl et al discloses an ion treatment electrode per se having a porous polymer substance with a conductive coating.

U.S. Pat. No. 3,163,166 to Brant et al discloses an iontophoresis device in a fixed interfitting structural housing, which is designed to be hand held in operation.

U.S. Pat. No. 2,493,155 to McMillan discloses an iontophoretic device which is strapped or taped to the body. The device is electrically operatively connected to an external controlled circuit source.

U.S. Pat. No. 4,239,046 to Ong is directed to an iontophoretic electrode construction per se including electrically conductive respective hook and knitted filaments for attachably detachable electrode connection.

U.S. Pat. No. 4,273,135 to Larimore et al is directed to a biomedical electrode per se in which the conductive material is formed of a cohesive, conformable, non-ionic hydrophilic synthetic polymer, so as to provide an essentially dry electrode.

U.S. Pat. No. 4,243,052 to Bailey is directed to a disposable electrode per se which combines a fabric backing and a conductive mesh layer laminated thereto, and a conductive polymer adhesive which interfaces the conductive mesh and which contacts the skin of the patient.

Also, U.S. Pat. No. 4,367,745 to Welage relates to an electrically polymeric conductive composition per se for interfacing between the skin and the electrode plate of a biomedical electrode.

None of the above-referenced devices disclose an electrophoretic and/or electro-osmosis bandage or applicator for the non-invasive transcutaneous delivery of a medicament which is a self-contained, self-adhering unit, in which the combination of elements including battery, a current regulating source, a medicament solution or reservoir, and an adhesive conductive lip are integrally connected by means of a flexible polymeric electrically conductive cover. Additionally, there is no teaching of an applicator or bandage-like transdermal drug delivery system in which specialized structural configurations compensate for one's movement and skin stretch so as to preclude loosening or "hot spots", or of incorporating a third or feedback electrode in the patch or applicator for regulating the drug dosage.

Other problems with such prior art devices were that they were bulky and lacked the necessary drug delivery rate control.

Another significant problem associated with such prior art devices is that the user, in wearing the device over the course of a few days caused the applicator patch to fall off because of one's movement during the day or by showering, perspiration, etc. These prior art devices did not provide for any structures which compensated for one's body movement, nor did they preclude the "peeling" effect. Moreover, no control means was provided for the regulation of administering the drug.

SUMMARY OF THE INVENTION

The present invention therefore overcomes or reduces many of the drawbacks of the previous devices and methods for utilizing electrophoresis and/or electro-osmosis for the non-invasive transcutaneous delivery of a medicament.

This is accomplished in accordance with the principles of this invention by enclosing a complete electrophoretic and/or electro-osmosis drug administration system within an applicator virtually indistinguishable when in place from an adhesive bandage. The applicator is extremely shallow, capable of being made with a thickness of only about a tenth of an inch, and its length and width would be determined by the desired rate of drug delivery.

Preferred embodiments of this invention consist of a compact, multilayered applicator having unique "cellular-like" configurations, and having a first active layer containing medicament in contact with the skin, a second active layer superimposed on the first layer comprising a member to make electrical contact with the skin through the first layer, and a third active layer superimposed on the second layer comprising the electrical battery for the applicator in electrical contact with the second layer. Other layers may be included to provide other functions to be described. The applicator assembly is enclosed within a cover of electrically conductive material having a lip extending outwardly from the first layer and leaving the latter exposed and in contact with the skin. The underside of the lip is coated with an electrically conductive adhesive material so that when the applicator is mounted on the skin the cover material surrounded by the lip is in contact with the skin. The lip acts as a return electrode so that the skin completes the electrical circuit when the applicator is applied causing current to flow and medicament to be moved through the skin into the blood stream. A third electrode may be employed in a "loop" circuit to feedback a signal indicating when a desired dosage level is achieved in the blood serum, so that with such feedback loop a demand type applicator patch is achieved which regulates the drug dosage as desired. Also, an LCD or an electrochemically phototropic material (ECM) is incorporated in the circuitry of the device to serve as an indicator. With completion of the circuit, the indicator is activated so as to provide a positive indication that the drug is being delivered transdermally.

All the layers of the applicator may be made from conformable material so that the applicator is capable of being made large enough to be mounted over wide areas regardless of the contour involved.

Features which may be included in the applicator as described above include discrete cell construction, control electrode or probe and feedback loop circuit, a constant current flow limiting device and a device to terminate drug delivery after a predetermined period of time or quantity of drug.

It is thus a principal object of this invention to provide self-contained apparatus for the electrophoretic and/or electro-osmosis deposition of a medicament at a controlled rate.

Other objects and advantages of this invention will hereinafter become obvious from the following description of the preferred embodiments of this invention.

BRIEF DESCRIPTION OF THE DRAWINGS

FIG. 6 is a plan view of an alternate applicator similar to that of FIGS. 1 and 2, but incorporating a third or feedback electrode;

FIG. 7 is a sectional view taken along the line 7—7 of FIG. 6, and showing the applicator mounted on skin;

FIG. 8 is an electrical schematic of the circuitry embodying the third or feedback electrode and applicator shown in FIGS. 6–7;

FIG. 9 is an alternate applicator package construction wherein the battery and/or the medicament reservoir or pouch/pad containing the drug is inserted in the field at time of application to ensure freshness and longer life;

FIG. 10 is another modified construction wherein the battery is externally mounted to the applicator package;

DESCRIPTION OF THE PREFERRED EMBODIMENTS

Figure 1:
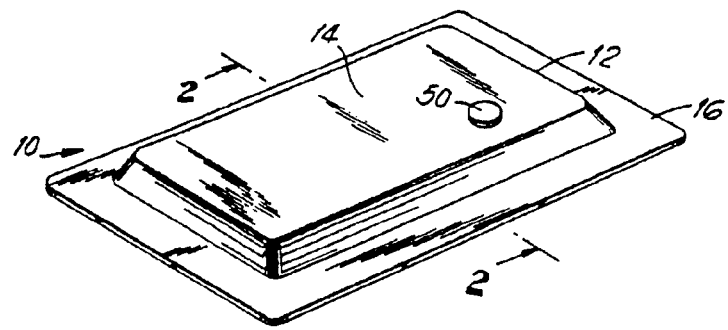
FIG. 1 is an isometric view of an applicator embodying the principles of this invention.
Figure 2:
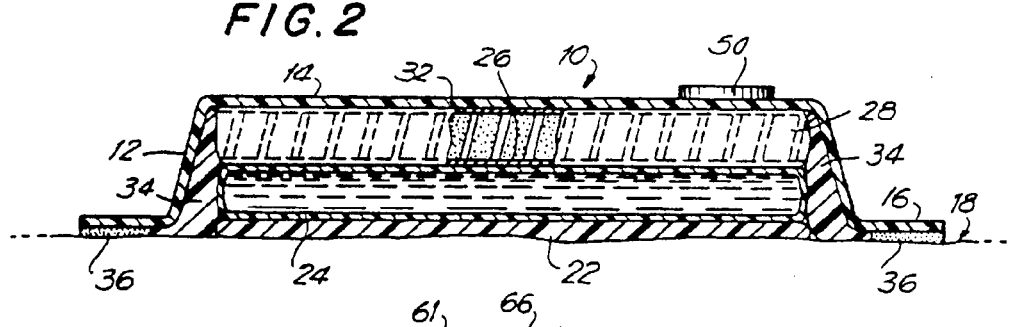
FIG. 2 is a cross-sectional view taken along the line 2—2 of FIG. 1, and showing the applicator mounted on skin.

Referring to FIGS. 1 and 2, applicator 10 consists of an outer cover 12 having a raised portion 14 and a lip 16 along the outer periphery. It is understood that applicator 10 can have any convenient shape or size, for example, square, rectangular, oval, circular, or tailored for a specific location on the skin, as long as this is a raised central portion to accommodate the rest of the electrophoresis and/or electro-osmosis unit to be described and the lip along its periphery.

As seen in FIG. 2, where applicator 10 is mounted on the surface of skin 18 of a patient, enclosed within the raised portion 14 of cover 12 are several layers to be described. The first layer is a microporous or semipermeable membrane 22 through which the medicament migrates to be deposited on skin 18. As will be noted from the following discussion, membrane 22 may not be needed, depending on the nature of the reservoir for the medicament.

The second layer consists of a flexible pad, pouch or other type reservoir 24 containing the drug to be administered. As is understood in the art, and shown in one or more of the U.S. patents identified above, reservoir 24 can be an impregnated pad or a pouch containing the drug of choice in solution or suspension, the walls of which are sufficiently dense to prevent leakage of the drug under ambient conditions, but sufficiently porous to permit migration of the drug, such as, for example, the charged particles or ions under the influence of the electric field imposed when utilizing electrophoresis. It should be noted that it would be appropriate to employ the microporous membrane 22 when leakage under ambient conditions could occur, for example, as a result of packing of the applicators for shipment or storage, fluctuating temperatures, and possibly puncture of the reservoir. Also, the use of the membrane 22 could depend in large measure on the nature of the medicament involved. In the alternative, reservoir 24 can consist of porous material in which the drug is impregnated rather than a pouch containing the liquid medicament.

The third or next layer above reservoir 24 is an extended contact 26 which could be incorporated as one face of battery 28 which is the next layer. Contact 26 could be any suitable conductive material, preferably body-conformable, to permit applicator 10 so as to be curved or bent to conform to the shaped surface of the skin. Suitable materials of this type are well known in the art and include electrically conductive polymers, preferably non-ionic. Carbon loaded or surface metalized plastics are also available for such use.

Battery 28 comprising the next layer can be made up of a group of cells internally connected in series to obtain the desired voltage necessary to obtain the electrophoretic action with the particular medicament, and orientation of battery 28 would depend on whether the charged (ionic) particles of the drug of choice are positive or negative. If the particles are negatively charged in solution or suspension, then contact 26 would be connected to the negative side of battery 28 as the skin will then be positive with respect to that contact and will attract the ions. With electro-osmosis, greater flexibility in design and structure is permissible as, for example, the pH of the drug solution is not important, since electro-osmosis is a physical phenomena, rather than a chemical phenomena. Moreover, the solution can be highly concentrated which is in contrast to that of an ionic solution, which requires high ion mobility and thus lower concentrations. However, with an entirely electro-osmosis unit, control of drug delivery is more difficult. Consequently, although both types of drug delivery systems are contemplated herein and come within the scope of this invention, the system utilized should be based upon drug chosen.

Both systems are combinable or can be used simultaneously to maximize the efficiency of the product or to make it possible to deliver non-ionic drugs and/or large rates of delivery.

With regard to battery 28, it should be noted that any conventional miniaturized battery cells now generally available can be employed, arranged and connected in series to obtain the desired operating voltage. In addition, the technology now exists for batteries which are made up of very thin, flexible sheets of a conductive polymer with high surface areas relative to thickness to provide adequate current densities. One such so-called plastic battery is described in "Batteries Today", Autumn 1981, pages 10, 11 and 24. When such a battery is employed, sheets may be layered to place the cells in series, and an effective compromise between number of sheets and surface areas of sheets is to layer them in a diagonal as shown somewhat schematically in FIG. 2. Of course, battery selection would ultimately depend on such factors as the degree of conformability desired, voltage and current densities required for a specific application, and time to discharge.

Layered above battery 28 would be another contact 32 which could be similar in construction to that of contact 26 and connected electrically to the opposite side of battery 28.

Cover 12 which encloses all of the layers of applicator 10 is made from a flexible conductive plastic material such as a polymer impregnated with carbon or surface metalized plastic. Insulating material 34 fills the space between the side wall of raised portion 14 and the various layers contained therein.

An electrically conductive adhesive material 36 coats the underside of lip 16 so that applicator or device 10 may be placed on and adhere to skin 18 and make good electrical contact.

It will be seen that the above described arrangement in general forms a complete electric circuit from one side of battery 28, cover 12, adhesive material 36, skin 18, microporous membrane 22, liquid reservoir 24, and back to battery 28.

Figure 3:
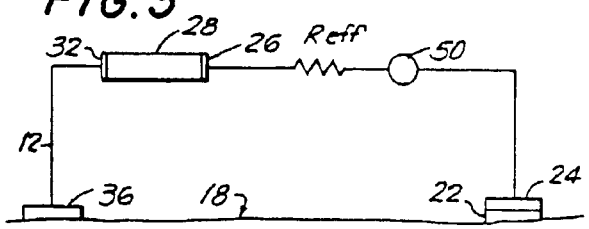
FIG. 3 is a schematic of electrical circuitry incorporated in the embodiment shown in FIGS. 1 and 2 showing an LCD indicator.

For a more particular description of the electrical circuit formed by the arrangement just described, reference is made to FIG. 3 wherein the circuit is shown schematically with numerals corresponding to the structure shown in FIGS. 1 and 2.

Battery 28 is connected through contact 32, cover 12, and adhesive layer 36 to skin 18. The other side of battery 28 is connected electrically through contact 26, liquid reservoir 24 and membrane 22 to skin 18 to complete the circuit. Resistor Reff represents the effective resistance of the complete circuit, including skin 18, the adhesive layer 36, cover 12, battery 28 and its contacts 26 and 32, as well as reservoir 24 and membrane 22. In a system of this type, one of the aims is to establish a very low specific rate of current flow so that the medicament will be deposited slowly over a long period of time. Current flow of down as low as 0.0001 ampere per square centimeter of skin surface below membrane 22 is a typical current which may be selected for the application of a particular drug. Electrical resistance of the skin to current flow is of the order of 6–9 K ohms and is roughly independent of the distance between the points on the skin where electrical contact is made. This is because skin electrical resistance is largely that of resistance to penetration, the current flowing through the fluids of the body in which electrical resistance is very low. Thus, in order to establish current flow at the rate indicated, by Ohm's law, it is seen that total resistance of the circuit using a 1.5 volt battery should be about 360 K ohms for each square centimeter of application. This resistance, the effective resistance, Reff, of the circuit can be built into any one component or combination of components of the circuit shown in FIG. 3, including the battery resistance, electrodes cover material, etc. In addition, if desired, in order to maintain current flow constant over the full period of operation a constant current limiting device can be made integral with and a part of conductor 26, or any other part of the circuit where it is found convenient to do so.

Figure 4:
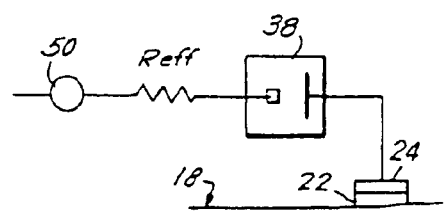
FIG. 4 is an alternative arrangement for the circuit shown in FIG. 3.
Figure 11:
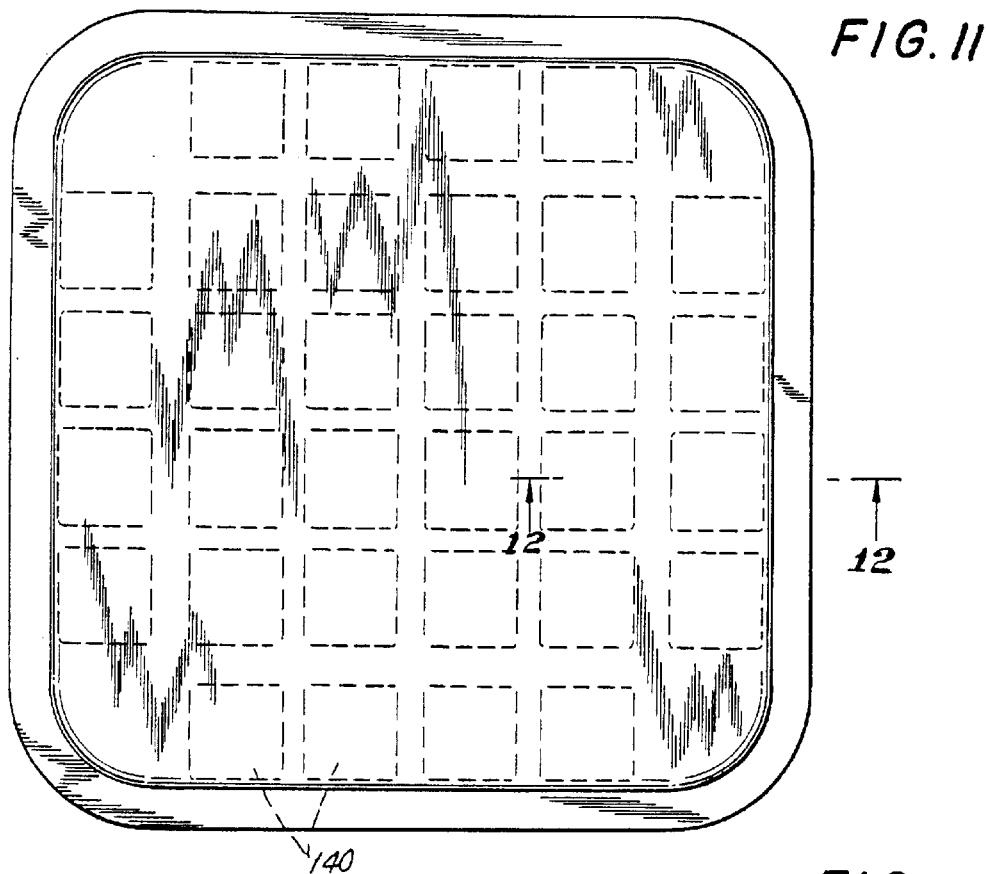
FIG. 11 is a plan view of another embodiment of the applicator wherein separate small patches are employed in the applicator construction.
Figure 12:
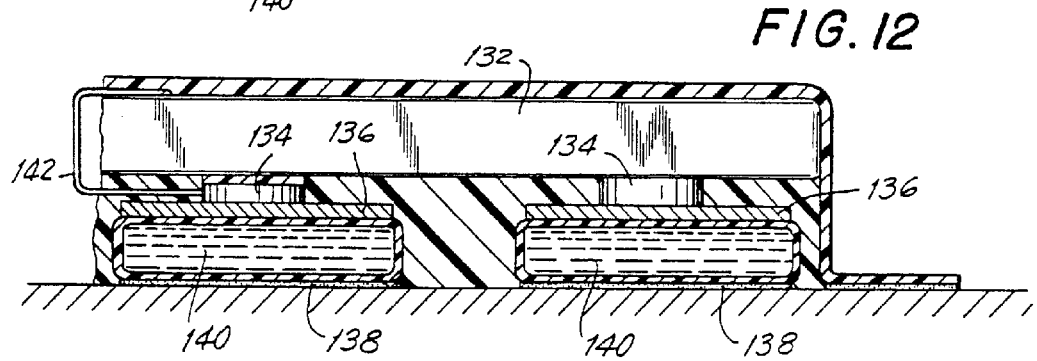
FIG. 12 is a sectional view taken along the line 12—12 of FIG. 11, and showing the applicator on skin.

Furthermore, as indicated schematically in FIG. 4, applicator 10 may be designed to incorporate a provision to insure that the deposit of medicament will cease after a given period of time or after a certain quantity of drug is administered. This can be accomplished by inserting in a circuit an integrating device such as a reverse plating cell 38. Cell 38, as is known in the art, comprises a pair of electrodes on which one is a coating of material to be transferred to the other electrode. When all of the plating material is deposited, after a predetermined period of time based upon the thickness of the original coating has lapsed, or integrated current flow representing the desired quantity of drug to be delivered, there is a large increase in internal resistance resulting in a substantial drop of current flow and an effective halt to drug migration. Such a device can be employed to establish in advance the period of time over which the medicament is to be applied or, as noted above, the quantity of the drug to be delivered. Cell 38 is a relatively high resistance device and could provide for much of the high resistance required for the operation of applicator 10.

Cell 38 may be made a part of contact 32 or be inserted between contact 32 and cover material 14. In addition, provision may be made for current flow to be built up gradually to avoid any shock to the recipient of the drug.

In FIGS. 1–4, there is shown liquid crystal display (LCD) 50 which is incorporated in the structure and circuitry of device 10. LCD 50 is designed so that it will cause a change in the light appearance only at and with the constant prescribed current of device 10. That is, with a completed circuit at such constant current, the prescribed dosage of medicament is being transcutaneously administered to the user, and LCD is light indicating so as to give a positive indication of this drug adminstration. In the event of (1) a broken circuit, such as a loosening of the conductive lip from the skin surface, (2) a dissipated or faulty battery, or (3) depletion of the medicament, so as to cause a failure of the constant current, the LCD will not show the liquid crystal display change, and the user will be informed that the prescribed drug is not being administered. The user is thus given a clear positive indication that either the drug is being properly administered or the drug is not being properly administered. In the latter event, the user merely removes the device and applies a new device, and upon the new application, the new LCD will be activated.

While the invention has hereinabove been described in the context of an LCD, light emitting diodes (LED) are also within the contemplation of this invention.

With the presence of indicator 50, the complete circuit is formed by skin 18, adhesive layer 36, cover 12, battery 28, indicator 50, contacts 32 and 26 filled reservoir 24, member 22 and resistor Reff.

Figure 5:
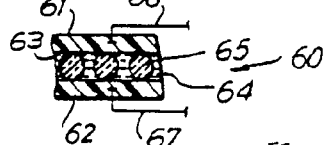
FIG. 5 is an enlarged sectional view of an alternate indicator embodiment.

Referring now to FIG. 5, there is shown a greatly enlarged sectional view of an alternate embodiment 60 for indicator 50. Indicator 60 comprises electroconductive polymeric upper and lower layers 61 and 62, respectively. Layers 61 and 62, in conjunction with non-conductive polymeric end caps (not shown), form a reservoir 63. Upper layer 61 has at least one transparent portion or is fully transparent for purposes hereinafter appearing. An electrochemically conductive phototropic material in the form of a solution or gel 64 is disposed in reservoir 63. A unilayer of silica particulates 65 is disposed in reservoir 63 so as to provide non-conductive spacing for layers 61 and 63.

Electrical leads 66 and 67 are provided to complete the circuit with battery 28 and contact 24, respectively.

Electrochemically phototropic or electrochromic materials will change color or appearance with the passage of the current through the material. Reservoir 63 is filled with such color changing material which is viewable by the user through transparent upper layer 61 of the present device. Suitable electrochemical phototropic materials include, by way of example, those ion change sensitive indicator dyes as disclosed in U.S. Pat. No. 4,013,414, granted Mar. 22, 1977 to Lavalee et al. By providing a highly polar condition in the indicator of the present invention, such ion change sensitive indicator dye color variations would be detected, thereby informing the patient that the medicament is being administered.

A most preferred electrochromic indicator device for use in the present invention electrodes is that disclosed in U.S. Pat. No. 4,066,366, granted Jan. 3, 1978 to Zeller, which disclosure is incorporated herein by reference thereto.

It is also within the contemplation of the present invention that the device's constant current be utilized to effect a change in electromotive force, temperature or other kinetic energy on a chemical and/or dye material which is color-responsive or phototropic with such change, so as to serve as an indicator. Such suitable dye materials are, by way of example, disclosed in U.S. Pat. No. 4,362,645, granted Dec. 7, 1982 to Hof et al.

Applicator 10 may be prepared in advance, in different sizes and shapes, sealed within a plastic pouch, with a protective strip over its exposed side. Different drugs can be incorporated for particular applications, batteries may be varied to meet specific current flow requirements, and of course the electrical orientation of each battery would depend on the particular medicament. In the use of the device, the protective strip is removed and the applicator placed on the skin where desired, such as behind the ear.

Current flow starts immediately along with migration of the drug.

The use of the invention as herein described makes it possible for the first time to provide for drug therapy over an extended period of time with a degree of control and accuracy which heretofore has not been possible or practical. The cost of such therapy using this invention is reduced significantly with the result that extensive use of the invention will have a favorable economic impact on medical care. The indicator now provides a positive degree of assurance to the user not heretofore available in body worn medicament dispensers.

In the embodiment of FIGS. 6–8, there is shown an applicator 70 having an outer cover 72 with a raised portion 74 and a lip 75 along the outer periphery. Within the raised portion 74 is a first layer 76, such as a microporous or semi-permeable membrane through which a drug is delivered by means of electrophoretic and/or electro-osmosis activity. As previously noted, in connection with FIGS. 1–2, this first layer may not be needed, depending upon the nature of the medicament and if it is carried by means of a pad or reservoir type pouch.

The second layer consists of a flexible pouch 78 (or pad or other reservoir) containing the drug. The pouch 78 precludes leakage, but is porous so as to permit drug migrations, be it by means of either or both of said delivery systems noted hereinabove.

The third layer above the pouch reservoir 78 is an extended contact 80 which may be part of one face of the battery 82 which is the next layer. The contact 80 is similar to that of contact 26 described with respect to FIGS. 1–2, and the battery 82 is likewise similar to those previously noted herein.

A further contact 84 above battery 82 is similar to that of contact 80 and same is connected electrically to the opposite side of the battery 82. The cover 72 encloses all layers of the applicator 70 including a third or feedback electrode 86 protruding or extending outwardly beyond the rectangular configuration of the applicator 70, and electrically connected to the contact 84 by means of conductor 88.

Insulating material 90 fills the voids between the side wall of raised portion 74 and the various layers, and also insulates the third or feedback electrode 86 and its wire conductor or lead 88 from coming into contact with any other components of the electrical circuit.

As shown in FIGS. 7, contact is made through the skin 90' to the electrically conductive adhesive v "electrode" material 92 which coats the underside of lip 75 so that the applicator device 70 is securely adhered in place on the skin 90' with good electrical contact. Such arrangement forms a completed electrical circuit from one side of battery (contact) 82, cover 72, adhesive material 92, skin 90', microporous membrane 76, liquid reservoir 78, and back to battery (contact) 82. The third electrode 86, which feeds back in a loop signal to an amplifier 94, is used as a control probe for sensing drug need. Such electrode or probe is suitably a conventional type which is, for example, ion-responsive and is provided with appropriate enzymes adhered on its surface 87 for sensing a specified chemical in the body or blood so as to regulate same. Such chemical may, for example, be sugar, insulin, or any other component which is desired to be sensed so as to determine the need for a particular drug. Thus, with such a simple feedback loop circuit, the amplified signal generated may be used to achieve a demand type drug delivery system, whereby drug dosage is controllable to a certain extent upon demand. It will be appreciated that the enzymes employed are capable of picking up the concentration of certain chemicals in the body which are desired to be controlled. Upon the enzyme sensing and detecting the particular chemical in the body, a charge or signal generated in the electrode probe is further amplified as required in order to provide a control signal to the applicator battery circuit for regulating the drug dosage to the desired level. Of course, it should be apparent that the electrode incorporates some sort of semi-conductor and/or field effect transistor which receives, amplifies and transmits the signal measured by the probe.

In FIG. 9, cover 72' is suitably constructed so as to enable the battery 82' and/or pouch 78' to be inserted into the raised portion 74' at the time of use. Either or both of the ends may form flaps 100 and/or 102 which are suitably provided with appropriate means for opening and closing the flaps. For example, minute hook and loop fasteners (shown only on the flap portions as 104) are merely exemplary of one fastening means, but other adhering means are also within the scope of the invention for enabling one or both flaps to be opened and closed. FIG. 10 simply illustrates an embodiment of the invention wherein the battery pack 110 is extremely mounted. Here, one of the battery terminals 112 is electrically connected to the conductive rim 113, and the other terminal 114 is in electrical contact with the reservoir pouch 116. With this construction, there is no need for any movable flaps, and the battery 110 is simply secured to the applicator 120 by any suitable adhesives at the time of assemblying the battery 110 to the applicator device 120.

Referring now to FIGS. 11–12 and 14–16, the applicator can be made with a plurality of cells or reservoir units 140. Such a type of construction lends itself to greater flexibility and ability of the applicator to conform to the contours of various parts of the body where such applicator package is to be used in the administering of drug dosages. Each cell or unit 140 is suitably surrounded by a non-conductive hydrophobic gel so as to insulate the cells or units 140 from each other. The battery 132 and one of its terminal electrodes is spaced, but electrically connected through a suitable resistor 134 to the layer 136. Between layer 138 and layer 136 is the drug reservoir pouch 140. The other resistor is suitably insulated from the same battery terminal side and is connected by means of a suitable lead 142 to the opposite terminal of the battery. Each cell or reservoir unit 140 exhibits the same structure which forms an overall grid pattern to the flexible applicator which can be made into any desired shape.

As shown in FIGS. 14–16, the shape may be formed by paired halves 150 and 152, as illustrated in FIGS. 14–15, respectively, with both halves together forming a single unitary applicator patch capable of delivering a single unit dosage of drug to one's body.

In an extreme example of a very flexible applicator patch, FIG. 16 shows a unit which forms "petal" like appendages 154 of a flower structure which likewise forms a unitary applicator package. In this embodiment, there are only eight cells or units as compared to the twelve cellular units of FIG. 15 and the eighteen cells of the embodiment of FIGS. 14, or the thirty-six cells of FIGS. 10–11.

Figure 13:
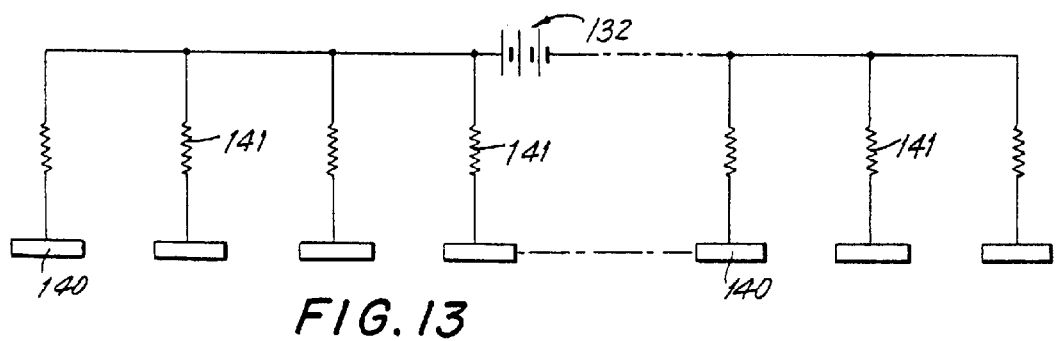
FIG. 13 is an electrical schematic of the circuitry for the applicator illustrated in FIGS. 11–12, and FIGS. 14–16 are plan views of further modifications of the applicator of FIGS. 11–12.

Schematically, the electrical circuits for these applicator packages are all the same, and thus is suitably shown in FIG. 13. As shown therein, the cells 140 form parallel circuits with suitable current regulating devices, such as constant current diodes, operational amplifiers or resistors 141 in series with each cell 140.

The present invention is further illustrated by the following tables illustrating examples which represent test data obtained from preclinical applicator patch models sized approximately 3"×4" and comprising a drug reservoir and a self-contained battery connected by wire to a resistor in series for maintenance of a constant current. The tests consisted of evaluation of serum levels of the drug TROBICIN at various time intervals such as 0, 1, 2, 4, etc. hours after continuous application of the device, in both rabbits and dogs.

The animal skins were shaved of fur to expose the skin and to a size to receive the applicator patches, and serum levels were analyzed for the Tobramycin using a radio immuno assay kit. Some of the tests were conducted with TROBICIN solutions of different pH.

In each of the experiments, the TROBICIN concentration was equal to 4 gm/37 ml (in solution with distilled or sterile water, which solution was equally applied to the positive and negative electrodes of the patches).

TABLE 1

Transdermal Administration of TROBICIN in Rabbits

| Rabbits Time | Control (No Power Drug in Patch) | | |
|---|---|---|---|
| | 1 | 2 | 3 |
| | Trobramycin Serum Levels (ug/ml) | | |
| 0 | 0 | 0 | 0 |
| 2 | 0 | 0 | 0.29 |
| 4 | 0 | 0.72 | 0.74 |
| 6 | — | | |

TABLE 2

Transdermal Administration of TROBICIN in Dogs

| Dogs Time | I | II |
|---|---|---|
| | Trobramycin Serum Levels | |
| | (ug/ml) | |
| 0 | 0.00 ug/ml | 0.00 ug/ml |
| 1 | 0.13 | 0.47 |
| 2 | 0.00 | 0.17 |
| 4 | 0.25 | 0.25 |
| 6 | 0.31 | 0.20 |

Additional experiments were conducted on rabbits with the drugs testosterone and aspirin.

TABLE 3

Transdermal Administration of Testosterone (radio-actively tagged) in Rabbits

| Rabbits (Average of 15 Rabbits) Hours | 0 | 1 | 2 | 3 | 6 |
|---|---|---|---|---|---|
| DPM (Disintegration per minute) | 0 | 27 | 69 | 73 | 98 |

TABLE 4

| Rabbits (Average of 5 Rabbits) Hours | 0 | 1 | 2 | 3 | 4 |
|---|---|---|---|---|---|
| Milligrams/ liter | 0 | 17 | 20 | 20 | 22 |

Although these results are representative of initial laboratory experiments, the protocol and procedures do not reflect an optimization of the device's capabilities. These tests do clearly verify the proof of principle in that the results of the serum RIA assays demonstrate that the devices did transdermally deliver Trobicin into the systemic system; and that in the case of both animals, Trobramycin was introduced into their systemic system by means of the activity of the patch.

In two other series of experiments by the inventor on himself using Trobramycin, the serum levels registered readings of 0.3 and 0.5 after 2 and 3 hours, respectively: and readings of 0.4, 0.12 and 0.5 after 1, 2 and 3 hours, respectively.

It should be noted that with respect to the transdermal delivery of a drug to the systemic system, among the varying factors electrophoresis as well as electro-osmosis may be of more or lesser significance depending upon a particular medicament and the desired rate of delivery.

It will be appreciated that each medicament exhibits an optimum mobility at a predetermined pH. The passage of electric current will induce a pH in the solution. This change could be beneficial or detrimental in which case a buffering agent is used to stabilize the desired pH at the optimal level.

The buffering agent or agents have a range of activity (e.g. a pH from say 4 to 5) and the medicament solution prior to the application of the patch could be at a pH which will assure long storage and shelf life, but not be the optimum pH for high drug mobility (drug delivery). The beginning of the current flow during the beginning of the use of the patch could start shifting or changing the pH into the range at which the buffer exhibits its buffering action. As the current continues its action on the solution, a predetermined point could be reached at which the buffer(s) is exhausted, thus reducing the medicament's mobility thereby terminating the drug delivery.

As shown in FIG. 13, there are a plurality of individual drug reservoirs, each one having its own current/timer solid state regulator. Such a construction allows a simultaneous or sequential delivery of drugs which cannot be mixed with each other and/or systemically delivered at the same time due to the possibility of mutual chemical reactions. Also, it is well known that certain drugs lose their chemical effectiveness if they are mixed with other drugs.

The electro-osmotic transfer or delivery of medicament always takes place at the positive electrode and the electrophoretic phenomena of medicament ion transport into the body is determined by the medicament's ion's polarity, i.e., it could take place at either electrode (negative or positive). If a drug is iontrophoretically delivered by the negative electrode, the same drug could be delivered at the same time by the positive electrode by employing electro-osmosis.

While only certain preferred embodiments of this invention have been described, it is understood that many embodiments thereof are possible without departing from the principles of this invention as defined in the claims which follow.

What is claimed is:

1. A conformable, pliable and relatively thin transdermal drug applicator for electrophoresis or electroosmosis of at least one medicament through the skin and into the blood stream of a patient comprising:
   (a) a plurality of juxtaposed flexible drug reservoir units formed with at least one medicament therein;
   (b) a conformable power source coupled to said plurality of juxtaposed flexible drug reservoir units, said power source having a battery and an electrical circuit formed to provide an electrical potential to said juxtaposed drug reservoir units;
   (c) a flexible, insulative and hydrophobic material surrounding said plurality of flexible drug reservoir units and said power source while leaving common sides of said plurality of flexible drug reservoir units adapted for contacting the skin, said flexible, insulative and hydrophobic material precluding shorting of said plurality of flexible reservoir units while aiding in providing flexibility to the applicator; and
   (d) a flexible cover surrounding said plurality of flexible reservoir units, said power source, and said flexible insulative and hydrophobic material while leaving common sides of said plurality of flexible reservoir units adapted for contacting the skin, said flexible cover being provided with a peripheral lip formed to releaseably cooperate with the patient's tissue such that said flexible cover is capable of compensating for movement of the skin during transdermal drug delivery, said flexible cover in combination with said plurality of flexible reservoir units, and said flexible insulative and hydrophobic material allowing said transdermal drug applicator to conform to the surface of a patient's tissue, the conformability of the transdermal drug applicator increasing with the number of said plurality of juxtaposed flexible reservoir units and amount of said insulative and hydrophobic material provided within the transdermal drug applicator.

2. The transdermal drug applicator of claim 1, wherein at least one of said at least two drug reservoir units including a plurality of drug reservoir units.

3. The transdermal drug applicator according to claim 2, wherein at least said one of said at least two drug reservoir units is positioned on one electrical pole side of said battery means and another of said at least two drug reservoir units is positioned on the other electrical pole side of said battery means.

4. The transdermal drug applicator according to claim 2, wherein said plurality of drug reservoir units form an overall grid pattern forming at least one applicator section, (whereby said applicator may be conformable to the contours of the body).

5. The transdermal drug applicator according claim 4, wherein said at least one applicator section is configured as a rectangle.

6. The transdermal drug applicator according to claim 5, wherein said rectangle is a square.

7. The transdermal drug applicator according to claim 4, wherein said at least one applicator section is a plurality of applicator sections.

8. The transdermal drug applicator according to claim 7, wherein said plurality of applicator sections is a pair of applicator sections forming a unitary applicator.

9. The transdermal drug applicator according to claim 8, wherein said pair of applicator sections are configured as a pair of rectangles.

10. The transdermal drug applicator according to claim 8, wherein said plurality of applicator sections are configured as a pair of separate semi-ovals forming a single unitary applicator.

11. The transdermal drug applicator according to claim 4, wherein said plurality of applicator sections are configured as a plurality of petals emanating from a central area.

12. A conformable, pliable, and relatively thin transdermal drug applicator for electrophoresis or electroosmosis of at least one medicament through the skin and into the blood stream of a patient comprising:

(a) a plurality of juxtaposed flexible drug reservoir units forming a conformable network, at least one of said plurality of juxtaposed flexible drug reservoir units being configured with:
(i) at least one medicament;
(ii) a flexible circuit board having an electrical circuit and a battery, said flexible circuit board configured for electrically connecting said battery to said at least one medicament; and
(iii) a flexible, insulative and hydrophobic material surrounding said at least one medicament and said flexible circuit board while leaving a side of said medicament and said flexible drug reservoir units adapted for contacting the skin, said flexible, insulative and hydrophobic material precluding shorting of said plurality of flexible reservoir units while aiding in providing flexibility to the applicator; and (b) a flexible cover substantially enclosing the applicator including said plurality of juxtaposed flexible reservoir units, said flexible circuit board, and said flexible insulative and hydrophobic material while leaving common sides of said plurality of juxtaposed flexible drug reservoir units adapted for contacting the skin, said flexible cover being provided with a peripheral lip formed to releaseably cooperate with the patient's tissue while allowing the applicator to be mounted and retained on the skin, said flexible cover in combination with said plurality of flexible reservoir units and said insulative and hydrophobic material allowing said applicator to easily compensate for movement of the skin, the conformability of the transdermal drug applicator increasing with the number of said plurality of juxtaposed flexible reservoir units and amount of said insulative and hydrophobic material provided within the transdermal drug applicator, while said applicator deforming and flexing to thereby conform to the contours of the patient's tissue and complete an electrical circuit through the skin via said flexible circuit board.

13. The transdermal drug applicator according to claim 12, wherein said reservoir units all have substantially the same structure.

14. The transdermal drug applicator according to claim 12, wherein one of said at least two reservoir units is positioned on one electrical pole side of said battery means and at least one of the other reservoir units is positioned on the other electrical post side of said battery means.

15. The transdermal drug applicator required to claim 12, wherein said lift means extends outwardly opposite applicator.

16. The transdermal drug applicator according to claim 15, said lip means extending in a plane generally paralleling a plane passing through the sides of said reservoir units exposed for contacting the skin of said patient.

17. The transdermal drug applicator according to claim 15, said lip means forming an uninterrupted peripheral zone circumscribing said applicator boundary.

18. The transdermal drug applicator according to claim 17, wherein said lip means is integrally formed with said means for covering and extends outwardly thereof forming a lateral annular flange about said applicator.

19. The transdermal drug applicator according to claim 12, wherein the shape of said reservoir units is selected from the group comprising rectangular, squarish, oval, half-oval and triangular shape.

20. A conformable, pliable, and relatively thin transdermal drug applicator for electrophoresis or electroosmosis of at least one medicament through the skin and into the blood stream of a patient comprising:

(a) a plurality of juxtaposed flexible drug reservoir units forming a cell-like network, said plurality of juxtaposed flexible drug reservoir units having at least one medicament in at least one of said plurality of juxtaposed flexible drug reservoir units;

(b) a power source coupled to said plurality of juxtaposed flexible drug reservoir units, said power source having a circuit including a battery, said circuit configured to electrically connect said battery to said at least one medicament in at least one of said plurality of juxtaposed flexible drug reservoir units;

(c) a flexible, insulative and hydrophobic material surrounding said plurality of flexible drug reservoir units and said power source while leaving common sides of said plurality of flexible drug reservoir units being adapted for contacting the skin, said flexible, insulative and hydrophobic material precluding shorting of said plurality of flexible reservoir units while aiding in providing flexibility to the applicator; and (d) a flexible cover substantially surrounding said plurality of juxtaposed flexible drug reservoir units, said power source, and said flexible insulative and hydrophobic material while leaving common sides of said plurality of juxtaposed flexible drug reservoir units adapted for contacting the skin, said flexible cover being provided with a peripheral lip formed to releaseably cooperate with the patient's tissue while allowing the transdermal drug applicator to be mounted and retained on the skin, said flexible cover in combination with said plurality of flexible reservoir units and said insulative and hydrophobic material allowing said applicator to easily compensate for movement of the skin, the conformability of the transdermal drug applicator increasing with the number of said plurality of juxtaposed flexible reservoir units and amount of said insulative and hydrophobic material provided within the transdermal drug applicator, while said applicator deforming and flexing to thereby conform to the contours of the patient's body and complete an electrical circuit through the skin via said circuit to allow migration of said at least one medicament from said plurality of juxtaposed reservoir units through said skin and into the blood stream of the patient.

21. The transdermal drug applicator of claim 20, in which said plurality of reservoir means are made from a microporous material whereby said at least one medicament provides an electrical path therethrough.

22. The transdermal drug applicator of claim 21; further including in said electrical circuit means to maintain constant current flowing during the period said at least one medicament is being delivered.

23. The transdermal drug applicator of claim 20, wherein said plurality of reservoirs are adjacently disposed.

24. The transdermal drug applicator of claim 20, wherein said plurality of reservoirs are spaced apart from each other.

25. The transdermal drug applicator of claim 20, wherein said means for separating said plurality of reservoir units from each other comprises a non-conductive hydrophobic gel.

26. The transdermal drug applicator of claim 20, wherein said plurality of reservoirs means are two.

27. The transdermal drug applicator of claim 20, wherein said overall grid pattern is configured as a rectangle.

28. The transdermal drug applicator of claim 20, wherein said overall grid pattern is configured a pair of halves.

29. The transdermal drug applicator according to claim 28, wherein each of said pair of halves is configured as a rectangle.

30. The transdermal drug applicator according to claim 28, wherein each of said pair of halves is configured as a semi-oval.

31. The transdermal drug applicator of claim 20, wherein said overall grid pattern is in the shape of a plurality of petals.

* * * * *